US00PP31721P2

(12) United States Plant Patent
Whitcomb

(10) Patent No.: US PP31,721 P2
(45) Date of Patent: May 5, 2020

(54) ***HIBISCUS SYRIACUS* PLANT NAMED 'WHIT XXI'**

(50) Latin Name: *Hibiscus syriacus*
Varietal Denomination: Whit XXI

(71) Applicant: Lacebark, Inc., Stillwater, OK (US)

(72) Inventor: Carl E. Whitcomb, Stillwater, OK (US)

(73) Assignee: Lacebark Inc., Stillwater, OK (US)

( * ) Notice: Subject to any disclaimer, the term of this patent is extended or adjusted under 35 U.S.C. 154(b) by 0 days.

(21) Appl. No.: 16/350,585

(22) Filed: Dec. 10, 2018

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
See application file for complete search history.

*Primary Examiner* — Anne Marie Grunberg
(74) *Attorney, Agent, or Firm* — Jeffrey L. Streets

(57) ABSTRACT

A new and distinct variety of *Hibiscus syriacus*, rose-of-sharon, named 'Whit XXI', particularly distinguished by having a compact, semi-dwarf, much branched upright elliptical shape, with dark green leaves, developing a high population of buds and flowers. Emergence of flower petals from the buds are at first dark red, then with expansion, red blotches on pink, then when fully opened the red blotches are no longer visible and flowers are pink. Flowers are sterile and long lasting.

4 Drawing Sheets

Genus, species: *Hibiscus syriacus*.
Varietal denomination: 'Whit XXI'.

BACKGROUND OF THE INVENTION

Field of the Invention

The present invention relates to a new and distinct variety or cultivar of the ornamental plant, *Hibiscus syriacus* commonly known as rose-of-sharon or althea.

Description of Related Art

*Hibiscus syriacus* is native to China and India, but history suggests seeds were transported by early traders over the Silk Road and dispersed over a wide area. The plant was first observed by western botanists in Syria, thus the species name *syriacus*. The plant grows well over a wide range of soils, moisture and other environmental conditions and is popular due to the flower show and long bloom time.

*Hibiscus syriacus* flowers on new growth so even when tops are killed or damaged by cold or are cut off, with the resumption of growth in spring, flowers soon follow. And, like other species of *Hibiscus*, each flower typically lasts only one day. However, a proliferation of buds allow the flower show to continue for 8 weeks or more. Flowers have little or no fragrance and most flowers fall cleanly leaving dried seed capsules with minimal effect on plant appearance.

In the USA, an assortment of seedlings have been selected, given varietal names and introduced into the nursery trade.

The new and semi-dwarf cultivar of *Hibiscus syriacus* claimed herein, which has been given the cultivar name 'Whit XXI', is a seedling selected from a block of about 4,000 seedlings which were 10 generations from the original parent used to begin this research in 1989.

This new and distinct *Hibiscus syriacus* was asexually reproduced near Stillwater, Okla. by rooting softwood cuttings taken from the original 'Whit XXI' plant near Stillwater, Okla. The asexually reproduced plants show all of the unique features that characterize this *Hibiscus*. As a further test, cuttings were taken from the asexually reproduced plants. These secondary cuttings rooted and grew the same as the parent, indicating that the unique features of this plant are stable through successive generations of asexual reproduction.

SUMMARY OF THE INVENTION

The plant of the present invention is a new and distinct variety of rose-of-sharon, *Hibiscus syriacus* which has been given the cultivar name 'Whit XXI' and is characterized by flower buds on short pedicels that at first appear red as they extend just beyond the calyx, then as expansion continues red shows as blotches on backs of first petals, then as the flowers fully open, the red and pinkish areas are on the backs of the outer array of petals and are no longer seen, leaving the full flower appearance a soft pink. The flowers are sterile and only occasional deformed reproductive parts can be found. The semi-dwarf, much branched plant is a profuse flower producer. For example, when the photo of the overall two year old plant growing in the field was taken, there were 13 open flowers and 68 flower buds sufficiently developed to show color. The plant may reach a height of 6 to 8 feet with age. The original 'Whit XXI' is now seven years old and has remained compact and free of disease.

Leaves are dark green, alternate, simple and broadly ovate to triangular with an irregular serrate margin, and occasionally irregularly lobed. Leaf surface is dark green and smooth.

Inflorescences are coarse spikes that may reach 12 to 16 inches long or more. Flower buds typically develop in each leaf axil.

Flowers are light pink when fully opened with five, occasionally six typical petals, and a multitude of petaloids arising from the receptacle. Details of flower bud color are provided above.

Flower buds and flowers are in abundance over the surface of the plant, as even lower branches typically have flower buds and flowers. Flowers begin opening at the base of the coarse spike and progress upward irregularly. Flower buds are visible as dark green conical whirls of five or six sepals fused into a more or less tubular calyx, then sepals are pushed back by the expanding flower, with the first exposure of the petals turning red, then as the petals extend further, red blotches develop on what will become the back of the primary petals, then disappearing from view with the fully opened flowers. Under Oklahoma conditions, flowering typically begins in late June and continues until mid to late October, depending on seasonal conditions and moisture. Because 'Whit XXI' is sterile, flowers remain attractive into the second day versus the typical one day which is typical of the species.

DETAILED BOTANICAL DESCRIPTION

Figure 1:
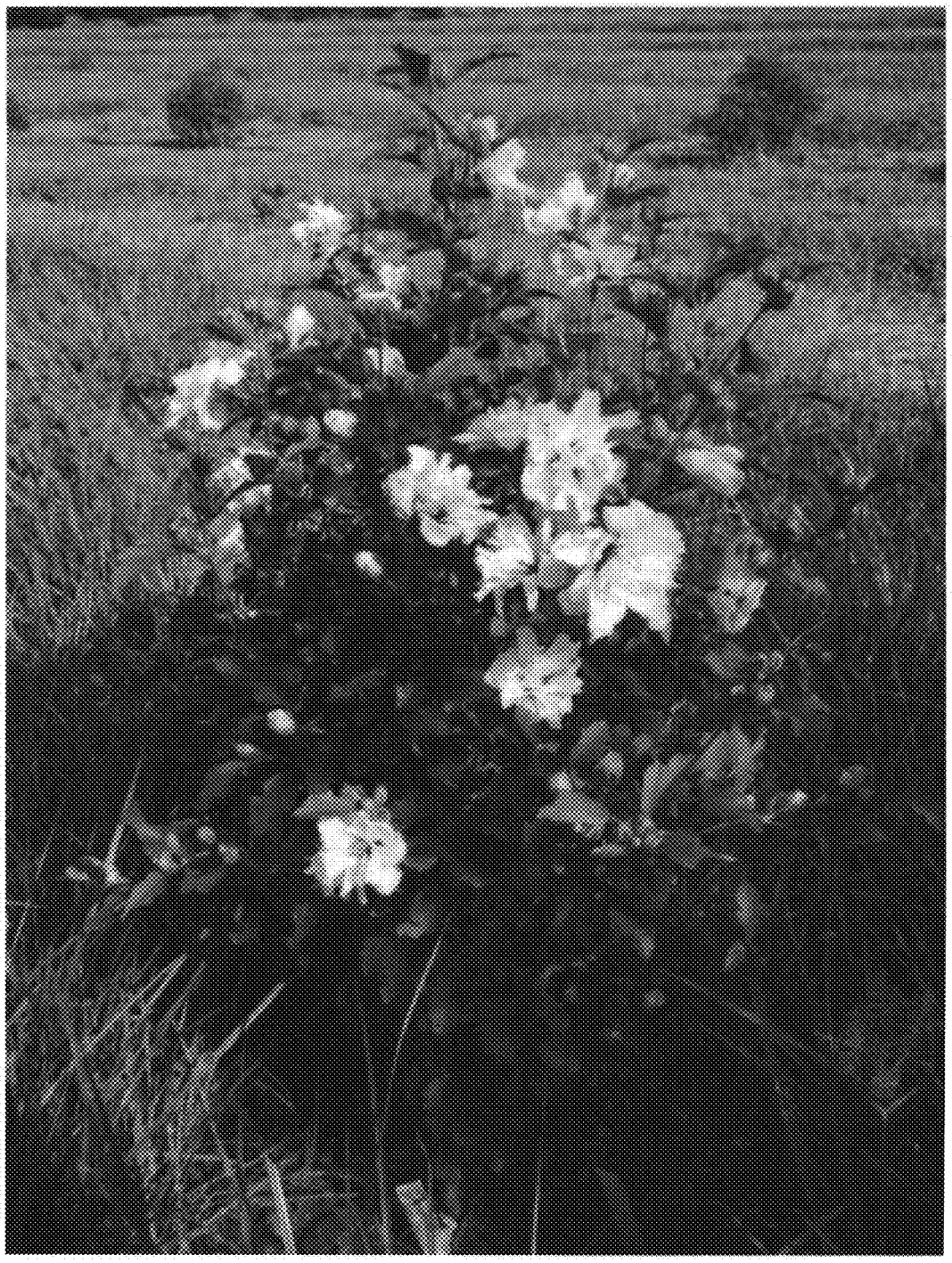
FIG. 1 is a full color photographic view of the new rose-of-sharon plant, 'Whit XXI' showing growth and prolific flowering habit after being propagated asexually from the parent two years earlier. On the day of the photo, there were 13 open flowers and 69 flower buds showing color.

The following description is of the new and distinct rose-of-sharon, *Hibiscus syriacus* plant which has been given the cultivar name 'Whit XXI'. Specific color designations set forth by number designations are in accordance with The Royal Horticultural Society Colour Chart (1966). General color recitations are consistent with ordinary American color terminology.

The rose-of-sharon cultivar 'Whit XXI' has not been observed under all possible environmental conditions. It is to be understood that the phenotype may vary significantly with variations in environment such as soils, temperature, light conditions and length of day without differences in genotype of the plant. The following botanical characteristics and observations are taken from plants when grown under normal outdoor conditions in north central Oklahoma. Unless otherwise noted, the following description is of plants propagated from the original parent plant grown in a field near Stillwater, Okla., but is also consistent with plants ranging from a few months to 18 months growing in containers in north central Oklahoma.

The plant:

*Type*.—Deciduous woody shrub with multiple stems and dense branching.

*Classification*.—Rose-of-sharon or althea, *Hibiscus syriacus*.

*Growth habit*.—The parent plant grew with a single upright stem and many low branches creating a broad ovate form.

*Origin*.—The original parent plant was a seedling growing in a fence row near Topeka, Kans. with flowers nearly all white but with a small reddish center. Since collecting seeds from that original parent in 1989, 10 generations of seedlings have been grown, with seeds being saved and planted from the best few plants in each generation. An open pollinated seedling was selected from a block of about 4,000 seedlings which were 10 generational descendants from the original parent. The relationship between the original plant and the current 'Whit XXI' plant are linked genetically but otherwise have few similarities. No genetics of any other plant or cultivar have been introduced into this breeding line.

*Propagation*.—The plant is easy to propagate from softwood cuttings placed under intermittent mist with the distinguishing characteristics of the asexually propagated offspring's remaining identical to the parent. When propagated from cuttings taken at tips of branches, a growth habit similar to the parent develops. However, if the tip of the cutting is removed at time of propagation, a broader based multiple stemmed plant beginning near the soil surface results.

*Size and shape*.—Growth of *Hibiscus syriacus*, 'Whit XXI' cultivar in an open field near Stillwater, Okla. is semi-dwarf relative to other seedlings from the same parent. For example, when 'Whit XXI' was 3 feet tall, most other seedlings from the same parent were 5 to 6 feet. Form is an upright broad elliptical shape, with an estimated height of 6 to 8 feet and a width of 4 to 5 feet at maturity.

*Hardiness*.—The new variety of rose-of-sharon has withstood temperatures of −8 degrees F. in the field with no injury. Based on its genetic heritage it is likely hardy in much of USDA Hardiness Zone 5.

*Pests and diseases*.—No diseases or insect problems have been observed on 'Whit XXI' cultivar or any of the rose-of-sharon seedlings as part of the plant breeding program in north central Oklahoma.

The flowers:

*Blooming period*.—Flower buds begin forming in mid-June with sustained warm temperatures, and flowers begin to open in early July in north central Oklahoma, and continues into mid-October, with variation due to seasons. Flowering continues during sustained heat as long as drought does not become severe. Rose-of-sharon, 'Whit XXI' is an exceptional producer of flowers and because the plant is sterile, flowers remain showy the full first day and into the second day. This extended flower show results from the absence of pollination and ovary expansion which causes flowers to drop on fertile seedlings. For example, in a block of 4,000 *Hibiscus syriacus* seedlings most flowers open in the morning and stay attractive most of the day before becoming less attractive and falling by late afternoon or evening.

*Petals*.—The outer array of flower petals are typically five, but occasionally six or seven, with an assortment of central petaloids ranging in numbers from 15 to 40 and in an array of widths and lengths. The primary five petals range in size from 1.25 to 3.0 inches long with irregular margins. The attitude of the outermost petals is approx. horizontal. Furthermore, the petal shape and undulation are variable in that, upon separating the petals of a flower, no two petals had the same shape or undulation. Similarly, the length of any eye zone extensions is variable in that, upon separating the petals of a flower, some petals are entirely the same color while other petals are slightly darker near the receptacle, with coloration related to light exposure.

*Inflorescences*.—Inflorescences are a coarse spike with flower buds on short pedicels developing in most leaf axils.

*Stamens*.—None, the flowers are sterile.

*Sepals*.—Calyx is made up of five, occasionally six sepals, each about ½ to ⅞ inches long, dark green, about 147-A or B, prior to flowers opening, turning variously greenish to yellow-green (no color match) and falling with the flowers.

*Buds and flowers*.—Flower buds progress from fully covered by the dark green sepals, about 147-B or C, to partial exposure of the flower petals which develop red blotches, about 53-B, C or D, and as more flower bud expansion proceeds showing previously fully red areas on backs of pink petals, about 49-A, B or C, to fully open flowers with flower petals and petaloids about 49-A, B or C. Basal areas of petals and petaloids are purple, about 187-A, progressing gradually to 187-D.

*Seeds*.—None, the plant is sterile.

Figure 2:
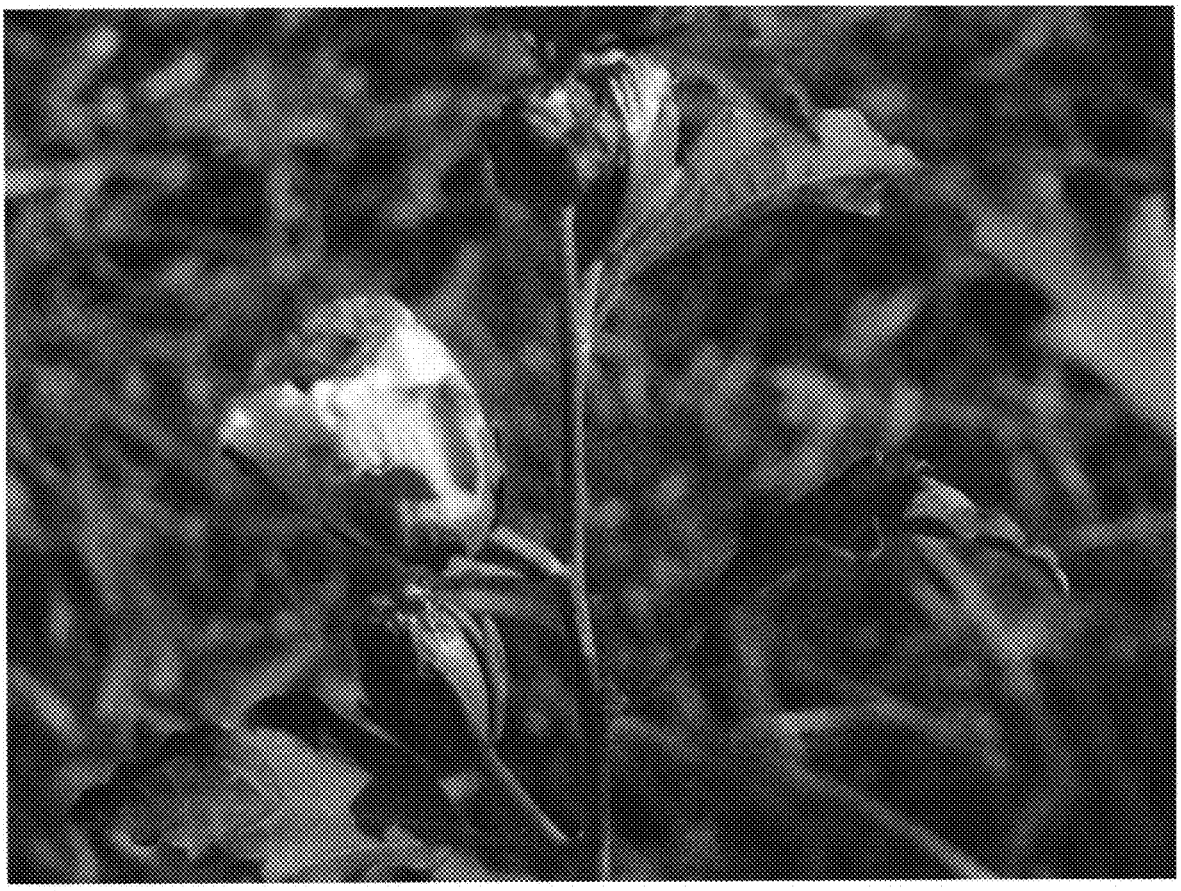
FIG. 2 is a full color photographic view of the new rose-or-sharon plant 'Whit XXI' showing typical flower bud coloration and early expansion before full flower development.
Figure 3:
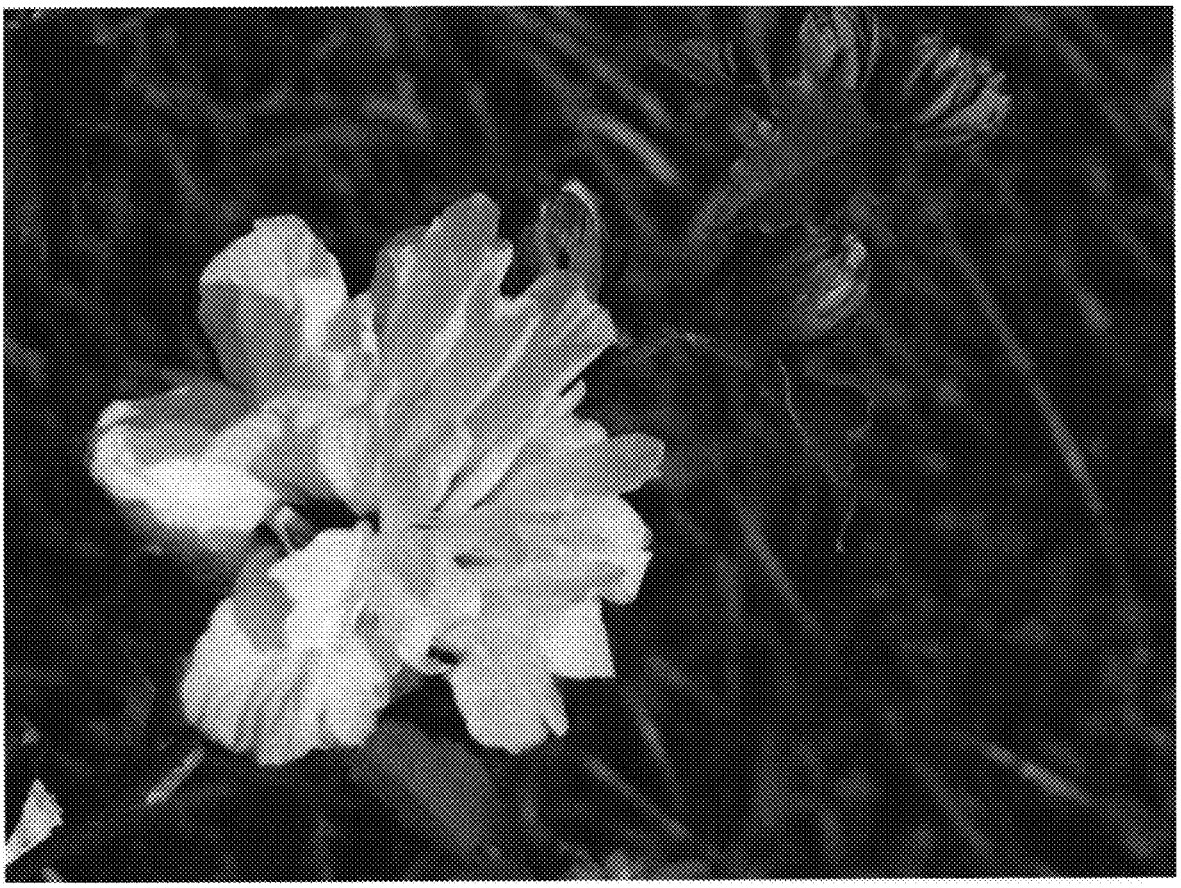
FIG. 3 is a full color photographic view of the new rose-of-sharon plant 'Whit XXI' showing a typical flower with irregular form, typical five primary petals and a multitude of petaloids that obscure the deformed or missing reproductive parts. Full flower development and positioning of primary petals obscures red blotches prominently visible on the developing buds.

*Pedicel*.—The pedicel length is variable as shown in FIG. 2, ranging from about 0.3 inches to 1.2 inches. The pedicel coloration is approx. 147-A or B.

Figure 4:
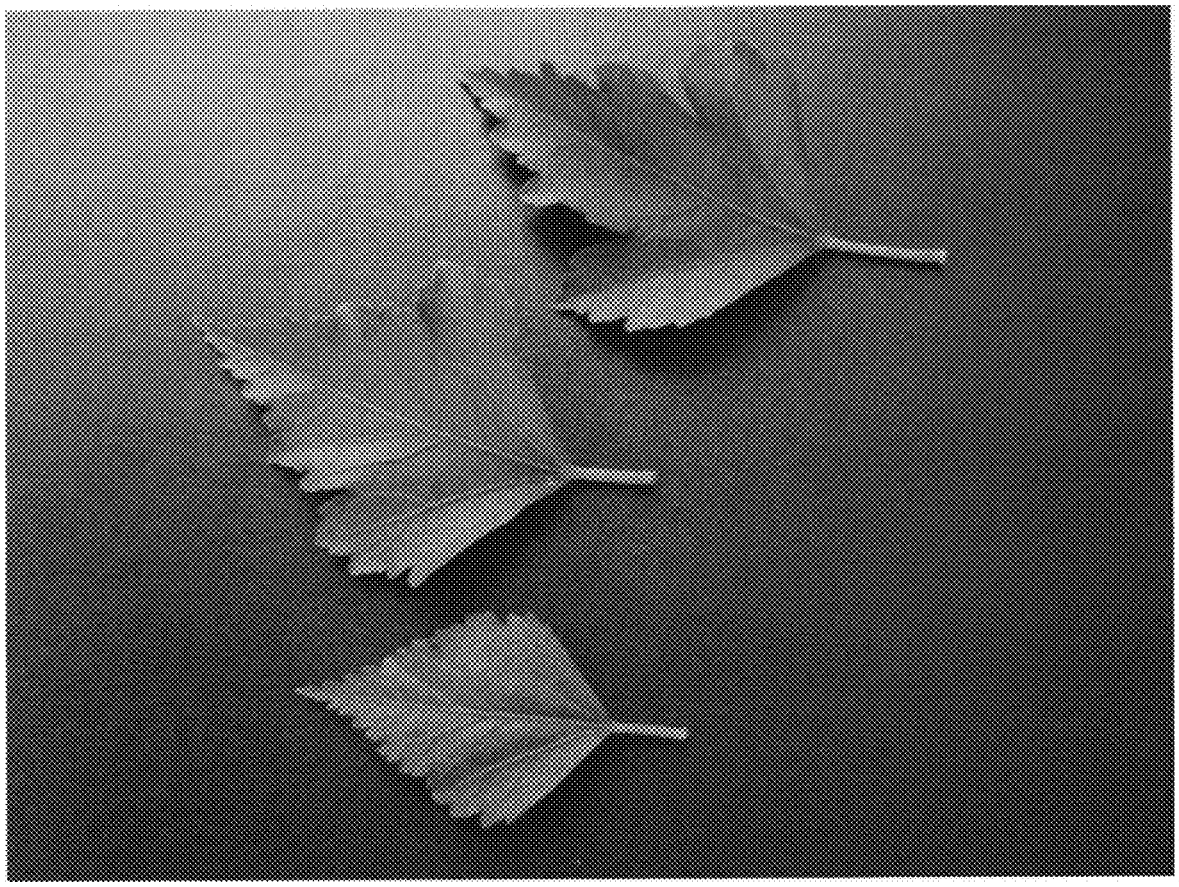
FIG. 4 is a full color photographic view of the new rose-of-sharon plant 'Whit XXI' showing the assortment of leaf shapes and leaf margins present among the foliage.

The foliage:

*Leaf shape*.—Leaves are alternate on the stem, simple, variously broadly ovate to triangular with an irregular serrate margin and occasionally irregularly lobed. The petiole length is variable from approx. 0.4 inches for leaves in full sun to approx. 0.8 inches for leaves in the shade. The shape of the leaf blade base is truncate. The leaf blade is variable, irregular serrate to doubly serrate. As shown in FIG. 4, the leaf blade margin incisions are variable.

*Leaf color*.—Upper leaf surface is dark green, 147-A or B is closest fit. Lower leaf surface is lighter, 147-B or C. The petiole coloration is approx. 147-A, B or C and variable with exposure to sun. The leaf venation coloration is widely ranging, from 147-B to D, depending on sun exposure.

*Leaf texture*.—Leaves are smooth, glabrous on both upper and lower surfaces.

*Leaf size*.—Leaves range from 1.5 to 2.5 inches long by about 3.4 to 2.5 inches wide, variable with age and growing conditions and location on the plant.

The branches and bark:

*Branch color*.—The current year branch coloration is approximately 197-A or B.

*Bark*.—Young and old stems are gray, about 197-A or B.

I claim:

1. A new and distinct variety of rose-of-sharon plant, substantially as illustrated and described.

* * * * *